US010092397B2

(12) United States Patent
Haddock et al.

(10) Patent No.: US 10,092,397 B2
(45) Date of Patent: Oct. 9, 2018

(54) INFRARED COMMUNICATION WITH AN OPTHALMIC DEVICE

(71) Applicant: Verily Life Sciences LLC, Mountain View, CA (US)

(72) Inventors: Joshua Naaman Haddock, Mountain View, CA (US); Dimitri Azar, Chicago, IL (US)

(73) Assignee: Verily Life Sciences LLC, Mountain View, CA (US)

( * ) Notice: Subject to any disclaimer, the term of this patent is extended or adjusted under 35 U.S.C. 154(b) by 0 days.

(21) Appl. No.: 14/985,315

(22) Filed: Dec. 30, 2015

(65) Prior Publication Data

US 2017/0189170 A1  Jul. 6, 2017

(51) Int. Cl.
| | |
|---|---|
| *A61F 2/16* | (2006.01) |
| *G02C 7/00* | (2006.01) |
| *H04B 10/114* | (2013.01) |
| *H04B 10/11* | (2013.01) |

(52) U.S. Cl.
CPC .......... *A61F 2/1624* (2013.01); *A61F 2/1613* (2013.01); *H04B 10/11* (2013.01); *H04B 10/1141* (2013.01); *A61F 2250/0001* (2013.01); *A61F 2250/0002* (2013.01)

(58) Field of Classification Search
USPC ....................................... 623/4.1, 6.22, 6.43
See application file for complete search history.

(56) References Cited

U.S. PATENT DOCUMENTS

| | | | |
|---|---|---|---|
| 6,120,538 A | 9/2000 | Rizzo, III et al. | |
| 9,002,463 B2 | 4/2015 | Tiedtke | |
| 9,081,208 B2 | 7/2015 | Blum et al. | |
| 2002/0072784 A1 | 6/2002 | Sheppard et al. | |
| 2003/0018383 A1* | 1/2003 | Azar ...................... | A61F 2/147 351/159.47 |

(Continued)

OTHER PUBLICATIONS

Simonov et al., "Liquid-crystal intraocular adaptive lens with wireless control", Optics Express, Jun. 1, 2007, vol. 15, No. 12, pp. 7468-7478.

(Continued)

*Primary Examiner* — David H Willse
*Assistant Examiner* — Javier Blanco
(74) *Attorney, Agent, or Firm* — Christensen O'Connor Johnson Kindness PLLC (57) ABSTRACT

Techniques and mechanisms for participating in a wireless communication with an implantable ophthalmic device. In an embodiment, an exterior of an ophthalmic device includes a biocompatible surface of an enclosure having control circuitry disposed therein. With the control circuitry, the ophthalmic device aids in sensing a condition at an eye or assists vision with the eye. In another embodiment, wireless communication circuitry is disposed in or on the enclosure, the wireless communication circuitry to participate in a communication of a wireless signal that is in an infrared wavelength range of the electromagnetic spectrum. Electrical signaling between the control circuitry and the wireless communication circuitry is based on the wireless signal. In another embodiment, the wireless signal is based on electrical signaling between the control circuitry and the wireless communication circuitry.

7 Claims, 6 Drawing Sheets

(56) References Cited

U.S. PATENT DOCUMENTS

| | | |
|---|---|---|
| 2006/0183986 A1 | 8/2006 | Rice et al. |
| 2010/0103369 A1* | 4/2010 | Pugh .................. A61F 9/023 |
| | | 351/158 |
| 2010/0211168 A1 | 8/2010 | Goertz et al. |
| 2011/0087306 A1 | 4/2011 | Goossen |
| 2012/0140167 A1* | 6/2012 | Blum .................. A61F 2/1624 |
| | | 351/159.34 |
| 2014/0043584 A1 | 2/2014 | Blum |
| 2015/0061990 A1 | 3/2015 | Toner et al. |

OTHER PUBLICATIONS

U.S. Appl. No. 14/842,703, filed Sep. 1, 2015, Wiser et al.
U.S. Appl. No. 14/937,135, filed Nov. 10, 2015, Haddock, Joshua N.
PCT/US2016/062269—International Search Report and Written Opinion, dated Feb. 16, 2017, 14 pages.

\* cited by examiner

INFRARED COMMUNICATION WITH AN OPTHALMIC DEVICE

BACKGROUND

1. Technical Field

This disclosure relates generally to ophthalmic devices, and in particular but not exclusively, relates to intraocular accommodation lenses.

2. Background Art

Accommodation is a process by which an eye adjusts its focal distance to maintain focus on objects of varying distance. Accommodation is a reflex action, but can be consciously manipulated. Accommodation is controlled by contractions of the ciliary muscle. The ciliary muscle encircles the eye's elastic lens and when contracted relieves tension applied to the lens via the zonules, causing the lens to relax, change shape, and thus alter its optical power.

As an individual ages, the effectiveness of the ciliary muscle degrades. Presbyopia is a progressive age-related loss of accommodative or focusing strength of the eye, which results in increased blur at near distances. This loss of accommodative strength with age has been well studied and is relatively consistent and predictable. Presbyopia affects nearly 1.7 billion people worldwide today (110 million in the United States alone) and that number is expected to substantially rise as the world's population ages.

Recent technologies have begun to provide for various devices that operate in or on a human eye to aid the visual focus of a user. For some types of these devices, an accommodating lens includes one or more elements and circuitry to apply an electrical signal to change a focusing power of the one or more elements. As successive generations of integrated circuitry continue to scale down in size and power consumption, there is expected to be an increased demand for additional functionality to be incorporated in medical devices such as accommodation-capable (or other) ophthalmic devices. Power consumption, cost and space are a few constraints that limit the ability to efficiently incorporate communications and/or other functionality in such devices.

BRIEF DESCRIPTION OF THE DRAWINGS

The various embodiments of the present invention are illustrated by way of example, and not by way of limitation, in the figures of the accompanying drawings and in which.

DETAILED DESCRIPTION

Embodiments described herein variously provide for communication with an implantable ophthalmic device using infrared (IR) signaling. An ophthalmic device according to one embodiment may operate to receive an IR signal from (and/or send an IR signal to) a remote device that, for example, is external to an eye in which the ophthalmic device is implanted. Based on such communications, the remote device may access the ophthalmic device to perform any of a variety of operations including, but not limited to, sending a control command, receiving a service (or other) request, reading stored data, updating software and/or firmware, changing one or more operational parameters or other settings, etc. Some embodiments are based on a realization that IR wavelengths may be used by an intraocular device—e.g., rather than radio frequency (RF) band signaling—since the eye is transmissive in an IR region of the electromagnetic spectrum. To provide for communication according to an embodiment, an ophthalmic device may include a light sensor (e.g. a photodiode) that is sensitive to signals in an IR band. Alternatively or in addition, such an ophthalmic device may include an IR light source to send signals from the eye.

Certain features of various embodiments are described herein with reference to an ophthalmic device that provides different levels of accommodation to aid vision with an eye. However, some embodiments are not limited to the providing of automatic accommodation, and such description may be extended to additionally or alternatively apply to any of a variety of other implantable ophthalmic devices. For example, a device according to another embodiment may provide only one level of accommodation. In another embodiment, an implantable device includes one or more sensors to detect a condition (e.g., a level of pressure) in or on the eye—e.g., in addition to, or in lieu of, the device aiding vision by the eye.

In the following description numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" means that a particular feature, structure, or characteristic described in connection with the embodiment is included in at least one embodiment of the present invention. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments.

Figure 1:
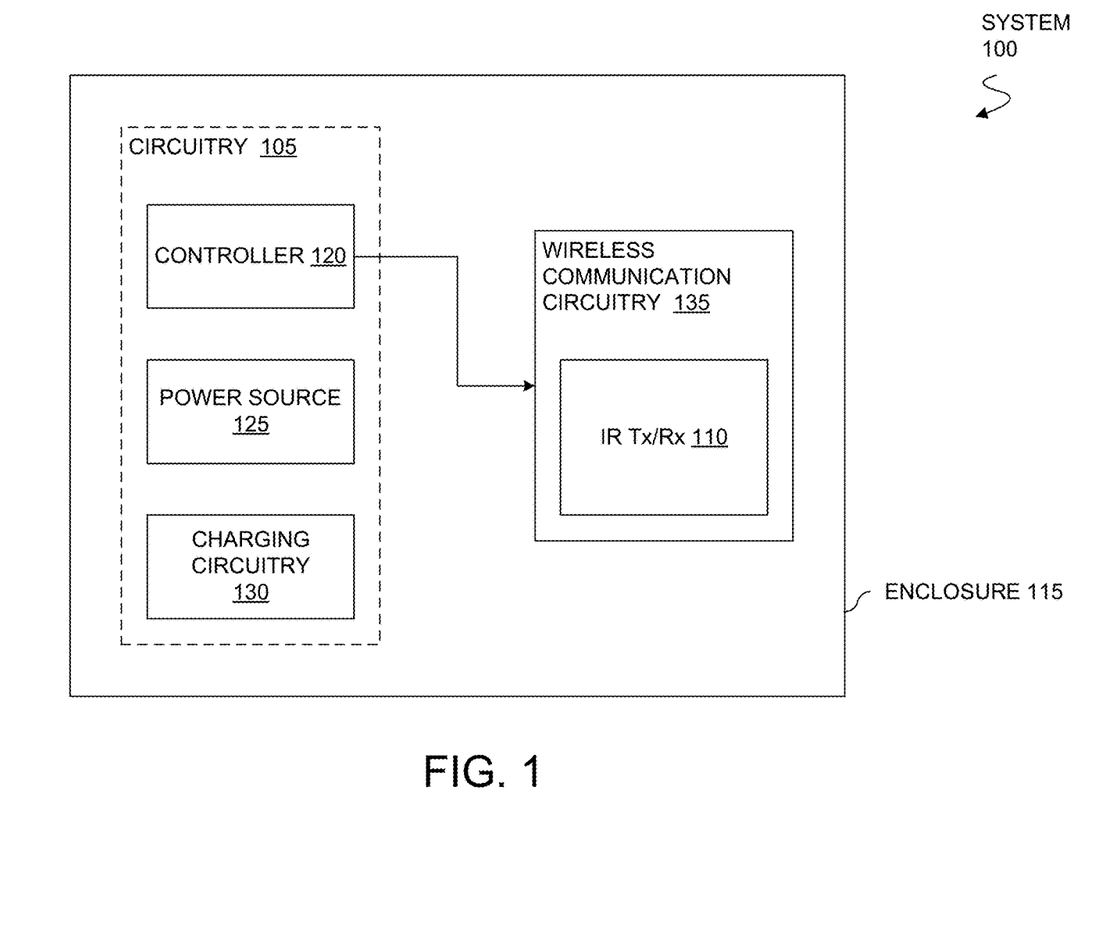
FIG. 1 is a functional block diagram illustrating elements of an ophthalmic system to exchange infrared signals in accordance with an embodiment.

FIG. 1 is a functional block diagram of an ophthalmic system 100 including an IR communication mechanism in accordance with an embodiment. Ophthalmic system 100 may be implemented as an intraocular lens ("IOL") that may be implanted into the anterior chamber, the posterior chamber, or other locations of a user's eye.

The illustrated embodiment of ophthalmic system 100 includes an enclosure 115 (or other housing structure) and circuitry 105 disposed therein. An exterior of ophthalmic system 100 may include a surface of enclosure 115 that is biocompatible to accommodate direct contact with an interior of a human (or other) eye. Such a surface of enclosure 115 may be formed by one or more biocompatible—and in some embodiments, optically transmissive (e.g., transparent, clear, etc.)—materials that accommodate implantation of the ophthalmic device. Examples of such materials include, but are not limited to, any of various biocompatible hydrogels, silicones, hydrophobic acrylics, fluorinated polymethacrylates and/or the like. In an embodiment, enclosure 115 includes a coating of biocompatible material that, for example, is formed by atomic layer deposition. Such materials may be adapted from those used in existing intraocular devices, for example.

Enclosure 115 may be a semi-rigid or rigid structure that surrounds—e.g., in at least a two dimensional plane—one or more components that are to aid in detection of a condition of an eye and/or to aid in vision with the eye. Such components may include circuitry, optics, one or more sensors and/or the like. Enclosure 115 may hermetically seal some or all such components. In one embodiment, an enclosure is itself an optical structure that, for example, has formed therein a dynamic optic for providing various degrees of accommodation. Alternatively, an enclosure may form an aperture that extends around optics, where the enclosure forms a seal around a perimeter of such optics.

The illustrated embodiment of circuitry 105 includes a controller 120 that, for example, may facilitate ophthalmic system 100 detecting a condition of an eye in which ophthalmic system 100 is implanted. Alternatively or in addition, controller 120 may operate to aid vision with the eye. Controller 120 may include logic coupled to coordinate the operation of the other components of ophthalmic system 100. Controller 120 may be implemented as hardware logic (e.g., application specific integrated circuit, field programmable gate array, etc.), software/firmware logic executed on a general purpose microcontroller, or a combination of both hardware and software/firmware logic.

Circuitry 105 may include or couple to any of a variety of additional or alternative circuit components, such as the illustrative power source 125 and charging circuitry 130. Power source 125 may be implemented using a variety of power storage devices including a rechargeable battery and/or capacitive elements. Charging circuitry 130 may be coupled to charge power source 125 and may include an inductive charging element, a photovoltaic element, a microelectromechanical systems ("MEMS") charging unit that uses natural motion to generate a current, or otherwise.

In an embodiment, enclosure 115 further has disposed therein and/or thereon wireless communication circuitry 135 that is electrically coupled to circuitry 105. Wireless communication circuitry 135 may include or couple to a wireless optical transmitter and/or a wireless optical receiver—e.g., as represented by the illustrative IR transmitter and/or receiver (Tx/Rx) 110. Such an optical transmitter and/or receiver mechanism may enable ophthalmic system 100 to transmit or receive a wireless communication comprising electromagnetic radiation that is in an IR band of wavelengths. For example, IR Tx/Tx 110 may include one or both of an IR light source and an IR light sensor. Light emitting diodes (LEDs), such as those used in television remote controls, are one example of light sources that may be adapted to facilitate wireless communication with an ophthalmic device according to an embodiment. Wireless communication circuitry 135 may further comprise circuitry to perform electrical domain processing (e.g., encoding, decoding, amplifying, buffering and/or the like) of signals in aid of such communication.

Certain embodiments are based on a realization that organic matter of an eye has good transparency characteristics for at least some infrared wavelengths. As used herein, "infrared" refers to one or more wavelengths that are longer than those of visible light, and less than that of a microwave—e.g., less than 1 millimeter (mm). An IR band may include some or all of wavelength ranges variously referred to colloquially as "near infrared," "medium infrared," and "far infrared." In one illustrative embodiment, IR Tx/Rx 110 participates in communication in an IR band that is from 700 nanometers (corresponding to a 430 THz frequency) to 1 mm (corresponding to a 300 GHz frequency). In another embodiment, such an IR band is between 700 nm and 2000 nm. In still another embodiment, the IR band is between 800 nm and 2000 nm. Such wavelengths may include those used by any of a variety of conventional semiconductor devices that, for example, emit in the 800 nm to 900 nm wavelength range. Alternatively or in addition, an IR band may include a range of wavelengths—e.g., including or otherwise near 1550 nm—such as that used by various telecommunication devices. It is noted that, as wireless communications approach 2000 nm or more in wavelength, absorption bands for water may begin to result in the eye itself attenuating IR signals.

With IR Tx/Rx 110, wireless communication circuitry 135 may participate in a wireless, IR communication between ophthalmic system 100 and a device (not shown) that is remote from ophthalmic system 100. For example, wireless communication circuitry 135 may be configured to participate in an exchange (e.g., unidirectional or bidirectional) of one or more signals with controller 120 and/or other logic of circuitry 105. Such an exchange may include wireless communication circuitry 135 sending to controller 120 a first electrical signal that is based on a first wireless communication received by an IR sensor (such as a photodiode) of IR Tx/Rx 110. Alternatively or in addition, the exchange may include controller 120 sending to wireless communication circuitry 135 a second electrical signal, wherein a second wireless communication transmitted by an IR emitter of IR Tx/Rx 110 is based on that second electrical signal.

In one example embodiment, IR Tx/Rx 110 receives a wireless command for controller 120 to turn off, turn on or otherwise change a functionality such as a level and/or type of accommodation provided by an accommodating lens (not shown) of ophthalmic system 100. However, any of a variety of additional or alternative types of communication may be exchanged via IR Tx/Tx 110, according to different embodiments. By way of illustration and not limitation, such communication may include ophthalmic device 100 downloading a firmware update, uploading log information, exchanging an error message or other alert signal, receiving an identifier of an operational mode to be configured, and/or the like. Wireless communication circuitry 135 (or other such logic of ophthalmic system 100) may be further configured to send and/or receive other wireless communications that, for example, are in a radio wavelength range (or any of various other non-IR ranges of the electromagnetic spectrum). For example, wireless communication circuitry 135 may further include a passive backscatter antenna (e.g., RFID tag) or an active antenna.

Figure 2A:
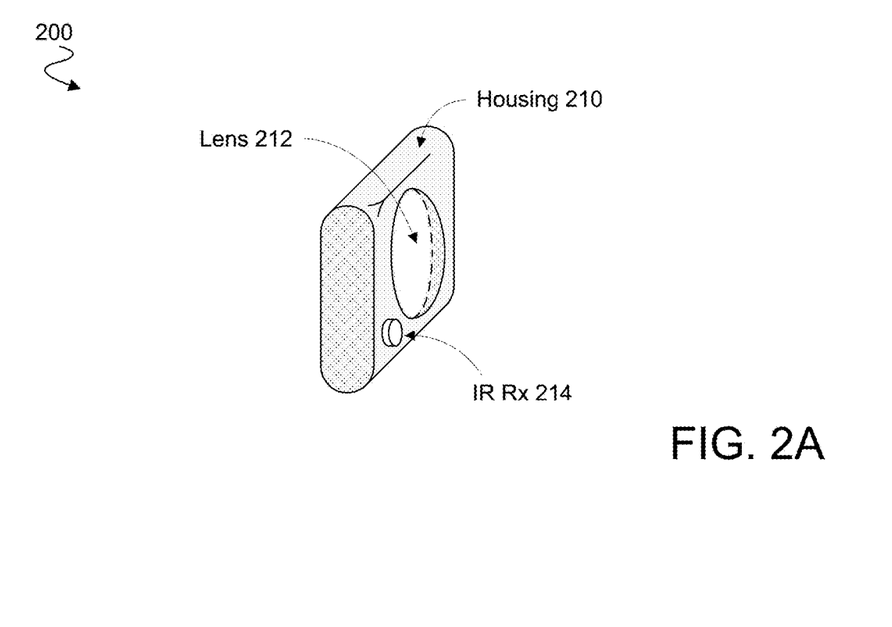
FIG. 2A is a perspective view showing elements of an ophthalmic lens device in accordance with an embodiment.

FIG. 2A shows a perspective view of an ophthalmic device 200 that supports optical IR communication according to an embodiment. Device 200 may include some or all features of ophthalmic system 100, for example. In the illustrative embodiment shown, housing 210 forms an aperture region in which is disposed a lens 212—e.g., where lens 212 has disposed therein a dynamic optic (not shown).

Circuitry disposed in housing 210 may aid in operation of such a dynamic optic and/or other mechanisms of device 200. Such circuitry may be coupled to receive—e.g., with the illustrative receiver IR Rx 214—a wireless communication including an electromagnetic signal in an IR band of wavelengths.

In response to the wireless communication, circuitry disposed in housing 210 and/or in lens 212 may selectively turn on, turn off or otherwise configure a functionality of ophthalmic device 200. For example, lens 212 may comprise liquid crystal, fluidic, electrowetting and/or other mechanism to selectively provide accommodation based at least in part on information communicated wirelessly to ophthalmic device 200 via IR Rx 214. Although shown as being disposed in an aperture region formed by housing 210, lens 212 may itself be at least part of housing 210 or, alternatively, substitute for housing 210—e.g., wherein IR Rx 214 is integrated with optics that form an exterior of ophthalmic device 200.

IR Rx 214 may receive IR signals transmitted by one or more IR light sources of a remote device (not shown). The remote device may include, for example, any of a variety of mobile (e.g., handheld, wearable, etc.) devices including, but not limited to, a smart phone, smart watch, tablet, laptop, earpiece or the like. In availing of an IR band for wireless communication, some embodiments variously enable the use of solid-state devices, such as light emitting diodes (LEDs), in an ophthalmic device. Data sent wirelessly to ophthalmic device 200 may be encoded in a digital format (e.g., as a series of light pulses) similar to one adapted, for example, from any of various television remote control techniques. Decoding functionality, such as that provided by wireless communication circuitry 135 and/or controller 120, may limit the possibility that some unintended source of spurious IR signals (e.g., a television remote control device) might cause unintended operation of ophthalmic device 200. IR receiver and/or transmitter functionality may allow for an ophthalmic device to participate in communication that is relatively long range—e.g., as compared to that provided by radio frequency identification (RFID), near field communication (NFC), Bluetooth or other radio band communication techniques.

Figure 2B:
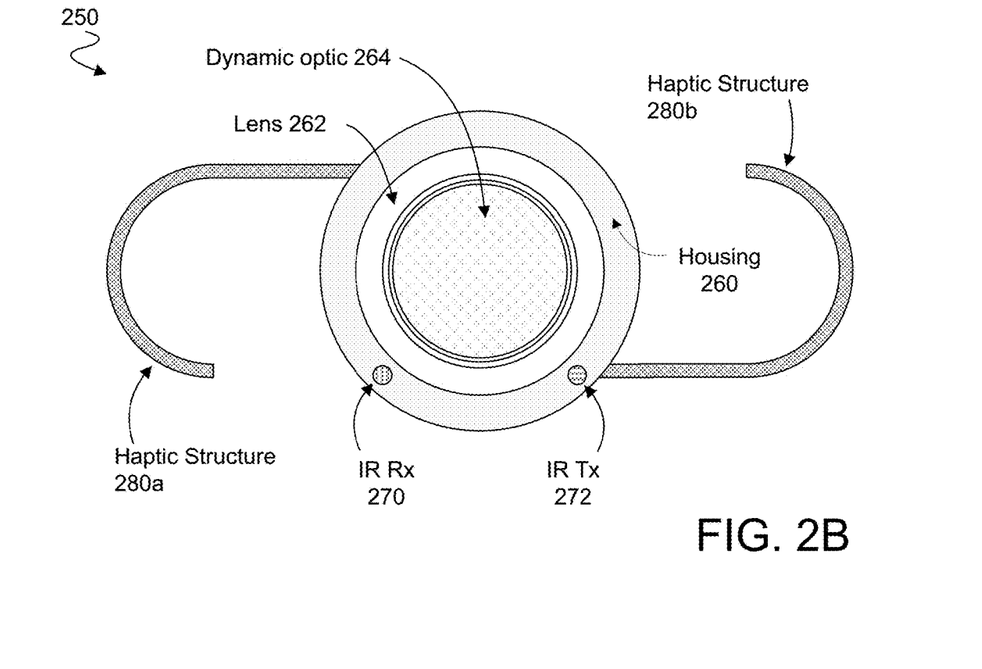
FIG. 2B is a plan view showing elements of an ophthalmic lens device to exchange infrared communications in accordance with an embodiment.

FIG. 2B illustrates elements an ophthalmic device 250 that supports wireless communication in an IR band according to another embodiment. Device 250 is one example of an embodiment—e.g., including some or all features of ophthalmic system 100—that provides both IR transmitter functionality and IR receiver functionality. In the illustrative embodiment shown, device 250 includes a lens 262 having disposed therein a dynamic optic 264. A housing 260 of device 250 may surround, and provide mechanical support for, lens 262. Alternatively, housing 260 may be part of (integrated with) an optical material of lens 262.

Device 250 may further comprise an infrared receiver IR Rx 270 including a sensor to detect for signals in an IR wavelength band. Alternatively or in addition, device 250 may comprise an infrared transmitter IR Tx 272 including a light emitting diode or other light source capable of outputting IR radiation. IR Rx 270 and/or IR Tx 272 may include circuitry adapted, for example, from any of various conventional integrated circuit mechanisms for exchanging IR signals. In some embodiments, device 250 further includes one or more haptic structures 280a, 280b to mechanically resist movement of device 250—e.g., to aid in keeping device 250 positioned within a desired location in an eye. The particular locations of IR Rx 270 and IR Tx 272 relative to each other and relative to lens 262 and haptic structures 280a, 280b is merely illustrative, and not limiting on some embodiments.

Figure 3:
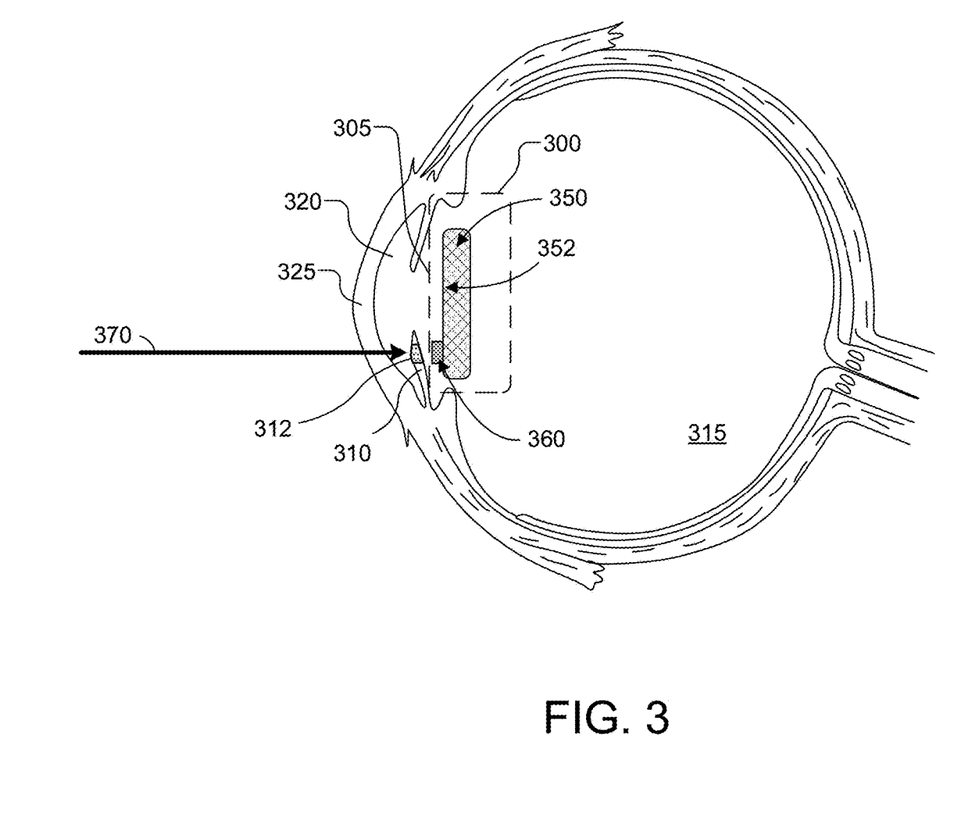
FIG. 3 is a cross-sectional illustration of an eye with an implanted intraocular device to participate in an infrared communication in accordance with one embodiment.

FIG. 3 is a cross-sectional illustration of an eye 315 having implanted therein an intraocular device 300 that provides for wireless communication in an IR band, in accordance with one embodiment. Intraocular device 300 may include features of ophthalmic system 100 and/or features of one of ophthalmic devices 200, 250, for example. Intraocular device 300 is illustrated as being implanted within the posterior chamber 305 behind an iris 310 of eye 315. However, intraocular device 300 may be implanted into other locations, as well, such as anterior chamber 320 disposed between iris 310 and cornea 325. In an embodiment, intraocular device 300 includes a housing 350 and IR Tx/Rx 360 disposed in or on housing 350. IR Tx/Rx 360 may provide for device 300 to transmit wireless IR communications and/or receive wireless IR communications. In an embodiment, IR Tx/Rx 360 is disposed at a side 352 of housing 350 that faces toward cornea 325—e.g., to receive an IR signal 350 via a straight path that extends from cornea 325 to side 352.

Some embodiments provide for ophthalmic device 300 to be implanted behind iris 310—e.g., where a surgeon may take steps during implantation of device 300 to ensure that IR radiation 370 reaches a light sensor of IR Tx/Rx 360. For example, in the configuration the ophthalmic device 300, radiation may be transmitted through a center of iris 310 or, alternatively, a surgeon may form a small hole 312 (or "iridectomy," distinct from the pupil), in iris 310, thus allowing IR radiation 370 to reach a light sensor of IR Tx/Rx 360. In such an embodiment, a location of IR Tx/Rx 360 in or on ophthalmic device 300—e.g., relative to a lens (not shown) of ophthalmic device 300—may facilitate implantation of IR Tx/Rx 360 in a region behind, and overlapped by, iris 310. In such an embodiment, IR Tx/Rx 360 may be further configured to be aligned to participate in an IR band communication via a signal exchanged through an iridectomy such as that represented by hole 312. In another embodiment the tissues of the iris 310 may not completely absorb all IR radiation and as such iridectomy 312 may not be required for IR radiation to reach and/or exit IR Tx/Rx 360.

Figure 4:
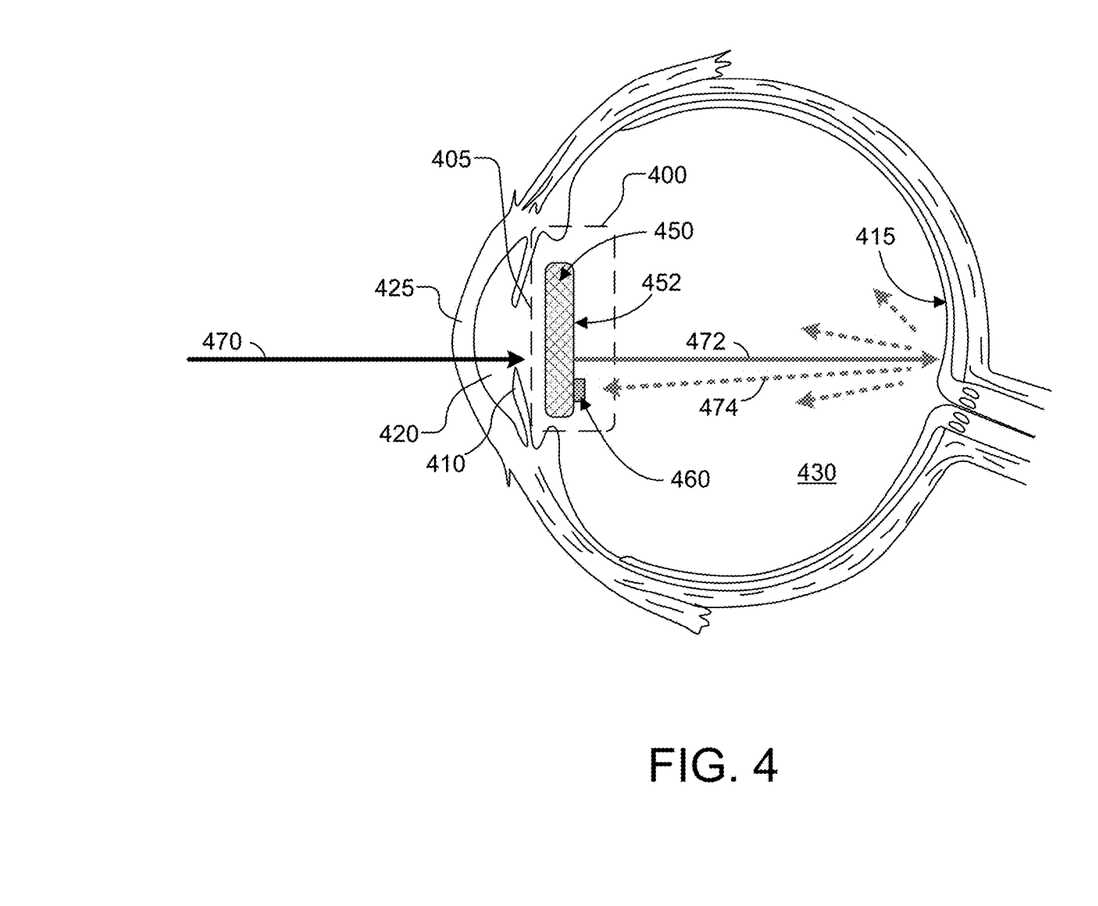
FIG. 4 is a cross-sectional illustration of an eye with an implanted intraocular device to participate in an infrared communication in accordance with one embodiment.

FIG. 4 is a cross-sectional illustration of an eye 430 having implanted therein an intraocular device 400 to support IR band communications according to another embodiment. Intraocular device 400 may include features of ophthalmic system 100 and/or one of devices 200, 250, 300, for example. Similar to device 300, intraocular device 400 may be implanted, for example, within a posterior chamber 405 behind an iris 410. Intraocular device 400 may include a housing 450 and IR Tx/Rx 460 disposed in or on housing 450. In the embodiment shown, IR Tx/Rx 460 is disposed at a side 452 of housing 450 that faces away from cornea 425 in a posterior direction toward the retina of eye 430. IR Tx/Rx 460 may itself be facing in a direction that is generally toward the retina. In such a configuration, IR Tx/Rx 460 may detect an IR signal that reflects off of part of the retina at the back 415 of eye 430. By way of illustration and not limitation, IR radiation 470 may be received at eye 430 via cornea 425. At least some portion 472 of IR radiation 470 may propagate past posterior chamber 405—e.g., through optics of device 400—and into the interior of eye 430. A reflection 474 of at least some of portion 472 may be direct back toward side 452 and detected by IR Tx/Rx 460. In some embodiments, detection of a diffuse reflection 474 may be enhanced with additional, larger and/or more sensitive photodetectors of IR Tx/Rx 460 at side 452.

Figure 5:
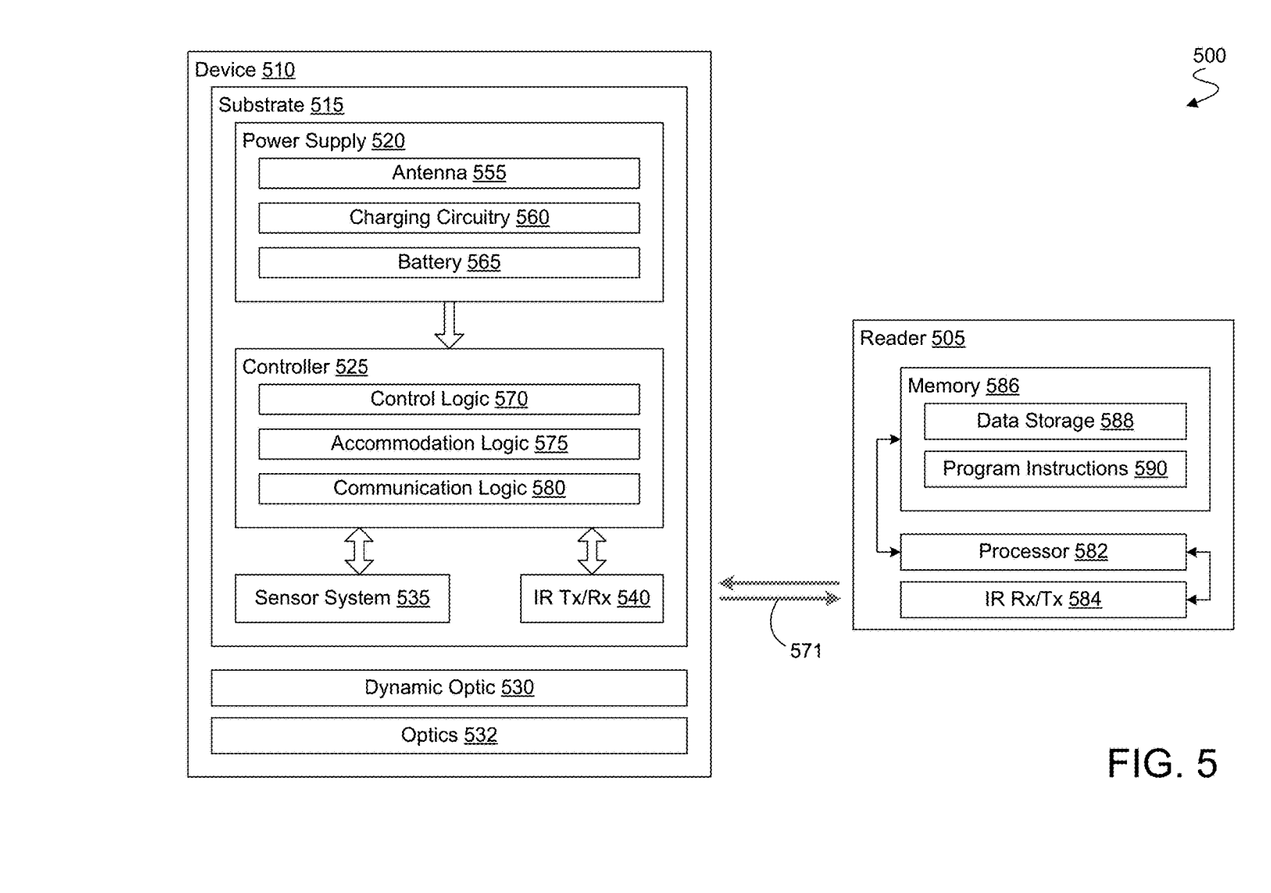
FIG. 5 is a functional block diagram of a system to exchange infrared signals between an ophthalmic device and an external reader, in accordance with an embodiment.

FIG. 5 is a functional block diagram of a system 500 for exchanging wireless communications in an IR wavelength band between an implantable ophthalmic device 510 and an external reader 505, in accordance with an embodiment. Device 510 may include features of ophthalmic device 100 and/or features of one of ophthalmic devices 200, 250, 300, 400, for example.

An exterior of device 510 may be formed by a housing that is biocompatible for implantation within an eye. For example, an exterior surface of device 510 may be formed by a biocompatible hydrogel, silicone, hydrophobic acrylic, fluorinated polymethacrylate and/or the like. Some embodiments are not limited to a particular biocompatible material of the housing, and any of a variety of conventional biocompatible materials may be adapted for incorporation into an ophthalmic device, according to certain embodiments.

A substrate 515 may be embedded within or surrounded by the housing to provide a mounting surface for circuitry, such as the illustrative power supply 520, controller 525, sensor system 535, a transmitter and/or receiver (e.g., the illustrative IR Tx/Rx 540), and various interconnects. The housing may include or have disposed therein other components such as static optics 532 and dynamic optic 530 (e.g., including a liquid crystal cell). However, any of a variety of additional or alternative components may be provided, according to different embodiments.

The illustrated embodiment of power supply 520 includes an energy harvesting antenna 555, charging circuitry 560, and a battery 565. The illustrated embodiment of controller 525 includes control logic 570, accommodation logic 575, and communication logic 580. The illustrated embodiment of reader 505 includes a processor 582, IR receiver and/or transmitter (e.g., the illustrative IR Rx/Tx 584) 540, and memory 586. The illustrated embodiment of memory 586 includes data storage 588 and program instructions 590.

Controller 525 may be coupled to receive feedback control signals from sensor system 535 and, for example, further coupled to operate dynamic optic 530. Power supply 520 may supply operating voltages to the controller 525 and/or the dynamic optic 530. IR Tx/Rx 540 may be operated by the controller 525 to communicate information to and/or from device 510. In one embodiment, IR Tx/Rx 540, controller 525, power supply 520, and sensor system 535 are all situated on the embedded substrate 515. Because device 510 includes electronics and is configured to be implanted within an eye, it is also variously referred to herein as an implantable ophthalmic device or an intraocular device.

To aid in accommodation and/or to facilitate implantation in the eye, optics 532 (and/or part of the housing) may have a concave surface. While implanted, an outward-facing surface of optics 532 may have a convex curvature. For example, optics 532 may be a substantially transparent curved disk shaped similarly to a contact lens. In some instances, optics 532 (and/or part of the housing) may be shaped to provide a predetermined, vision-correcting optical power, such as can be provided by a conventional artificial intraocular lens, spectacle lens, or contact lens.

Substrate 515 includes one or more surfaces suitable for mounting the sensor system 535, controller 525, power supply 520, and IR Tx/Rx 540. Substrate 515 may be employed both as a mounting platform for chip-based circuitry (e.g., by flip-chip mounting) and/or as a platform for patterning conductive materials (e.g., gold, platinum, palladium, titanium, copper, aluminum, silver, metals, other conductive materials, combinations of these, etc.) to create electrodes, interconnects, antennae, etc. In some embodiments, substantially transparent conductive materials (e.g., indium tin oxide) may be patterned on substrate 515 to form circuitry, electrodes, etc. For example, IR Tx/Rx 540 may be formed by depositing a pattern of gold or another conductive material on substrate 515. Similarly, interconnects 545 and 550 may be formed by depositing suitable patterns of conductive materials on substrate 515. A combination of resists, masks, and deposition techniques may be employed to pattern materials on substrate 515. Substrate 515 may be a relatively rigid material, such as polyethylene terephthalate ("PET") or another material sufficient to structurally support the circuitry and/or electronics within the housing. The housing may alternatively include an arrangement of multiple substrates rather than a single substrate. For example, controller 525 and power supply 520 may be mounted to one substrate, while IR Tx/Rx 540 and sensor system 535 are mounted to another substrate and the two may be electrically connected via interconnects.

In some embodiments, dynamic optic 530 is centrally positioned in optics 532 (and/or the housing of device 510) to apply optical accommodation to light being transmitted through both the eye and a center of optics 510. In some embodiments, device 510 further comprises one or more sensors (not shown)—e.g., one or more discrete photodetector sensors that are distributed in or on the housing to sense eyelid overlap. Although certain embodiments are not limited in this regard, sensor system 535 (and/or a sensor disposed in or on the housing) may additionally or alternatively include an electronic (e.g., MEMS-based) pressure sensor disposed in or on the housing of device 510. Data generated with such a pressure sensor may aid, for example, in clinical evaluation of an ophthalmic condition such as glaucoma.

In the illustrated embodiment, power supply 520 includes a battery 565 to power the various embedded electronics, including controller 525. Battery 565 may be inductively charged by charging circuitry 560 and energy harvesting antenna 555. Additionally or alternatively, power supply 520 may include a solar cell ("photovoltaic cell") to capture energy from incoming ultraviolet, visible, and/or IR radiation. Furthermore, an inertial power scavenging system may be included to capture energy from ambient vibrations. Charging circuitry 560 may include a rectifier/regulator to condition the captured energy for charging battery 565 or directly power controller 525 without battery 565. Charging circuitry 560 may also include one or more energy storage devices to mitigate high frequency variations in energy harvesting antenna 555. For example, one or more energy storage devices (e.g., a capacitor, an inductor, etc.) may be connected to function as a low-pass filter.

Controller 525 contains logic to choreograph the operation of the other embedded components. Control logic 570 may control the general operation of device 510, including providing a logical user interface, power control functionality, etc. Accommodation logic 575 may include logic for monitoring feedback signals from sensor system 535—e.g., to determine a current gaze direction or focal distance of a user, and to manipulate dynamic optic 530 in response to provide the appropriate accommodation. The auto-accommodation may be implemented in real-time based upon feedback from the gaze tracking, or permit user control to select specific accommodation regimes (e.g., near-field accommodation for reading, far-field accommodation for regular activities, etc.).

Communication logic 580 provides communication protocols for wireless communication with reader 505 via IR Tx/Rx 540. In one embodiment, communication logic 580 operates IR Tx/Rx 540 to exchange with reader 505 (e.g., to transmit and/or to receive) one or more wireless signals 571 that are in an IR wavelength band. In some embodiments, communication logic 580 may further support wireless communication in another (e.g., a radio) wavelength band. For example, communication logic 580 may further operates as a smart wireless radio-frequency identification ("RFID") tag that modulates the impedance of a communication antenna (not shown) for backscatter wireless communications. The various logic modules of controller 525 may be implemented in software/firmware executed on a general purpose microprocessor, in hardware (e.g., application specific integrated circuit), or a combination of both.

Ophthalmic device 510 may include various other embedded electronics and logic modules. For example, a light source or pixel array may be included in optics 532 to provide visible feedback to the user. An accelerometer or gyroscope may be included to provide positional, rotational, directional or acceleration feedback information to controller 525.

It is noted that the block diagram shown in FIG. 5 is described in connection with functional modules for convenience in description, but does not necessarily connote physical organization. Rather, embodiments of device 510 may be arranged with one or more of the functional modules ("sub-systems") implemented in a single chip, multiple chips, in one or more integrated circuits, or otherwise.

External reader 505 includes an IR Rx/Tx 584 to send and/or receive wireless IR signals 571 to/from device 510. External reader 505 also includes a computing system with a processor 582 in communication with a memory 586. Memory 586 is a non-transitory computer-readable medium that may include, without limitation, magnetic disks, optical disks, organic memory, and/or any other volatile (e.g. RAM) or non-volatile (e.g. ROM) storage system readable by the processor 582. Memory 586 may include a data storage 588 to store indications of data, such as data logs (e.g., user logs), program settings (e.g., to adjust behavior of device 510 and/or external reader 505), etc. Memory 586 may also include program instructions 590 for execution by processor 582 to cause the external reader 505 to perform processes specified by the instructions 590. For example, program instructions 590 may cause external reader 505 to provide a user interface that allows for retrieving information communicated from device 510 or allows transmitting information to device 510 to program or otherwise select operational modes of device 510. External reader 505 may also include one or more hardware components for operating IR Rx/Tx 584 to send or receive wireless signals 571 to/from device 510.

External reader 505 may be a smart phone, digital assistant, or other portable computing device with wireless connectivity sufficient to provide the wireless communication link 571. External reader 505 may also be implemented as a module that can be plugged in to a portable computing device, such as in an example where a communication link including signals 571 operates at carrier frequencies not commonly employed in portable computing devices. In some instances, external reader 505 is a special-purpose device configured to be worn relatively near a wearer's eye to allow the wireless communication link 571 to operate with a low power budget. For example, the external reader 505 may be integrated in a piece of jewelry such as a necklace, earing, etc. or integrated in an article of clothing worn near the head, such as a hat, headband, etc.

Figure 6:
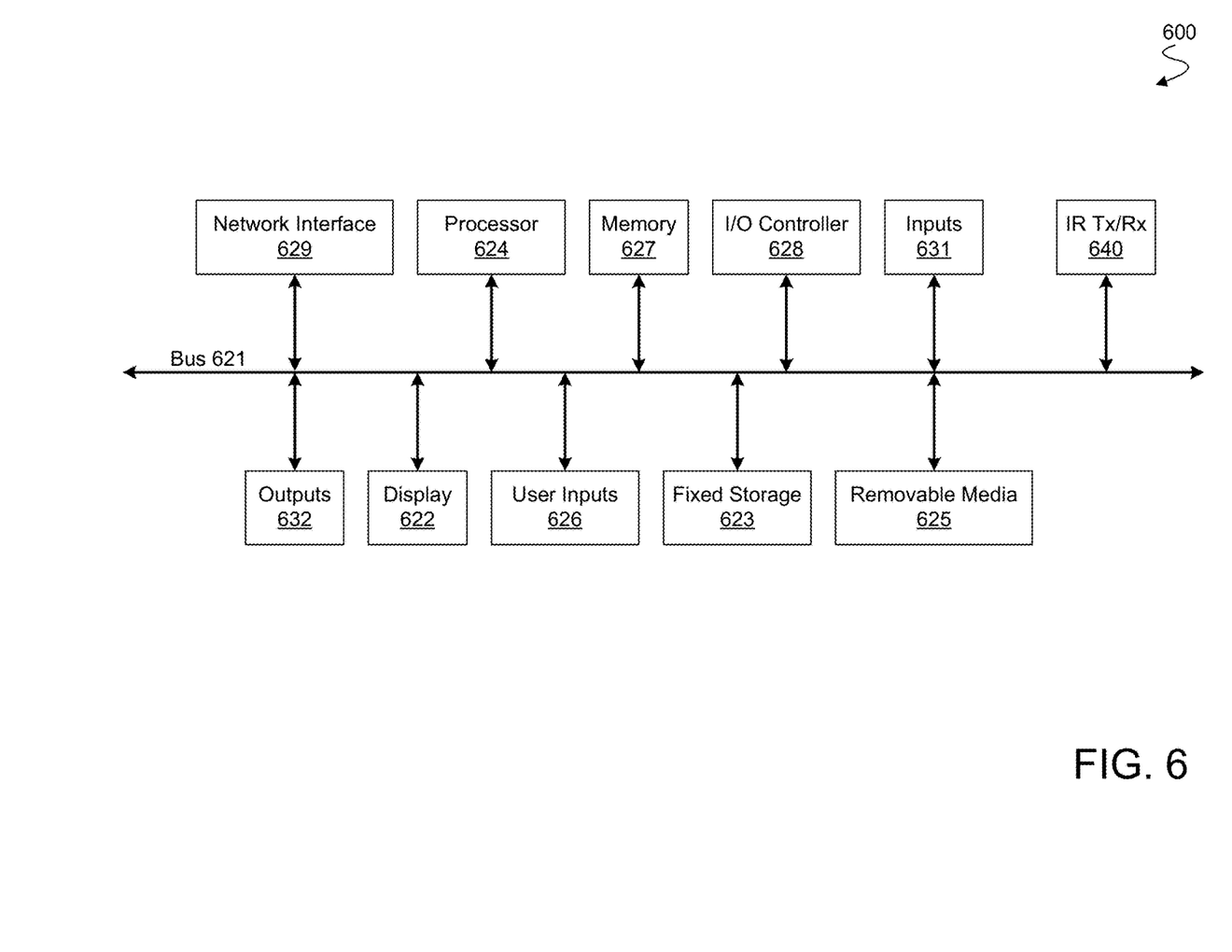
FIG. 6 is a functional block diagram illustrating elements of a device to participate in a wireless communication with an ophthalmic device according to an embodiment.

FIG. 6 shows an illustrative device 600 to participate in a wireless IR communication with an ophthalmic device according to an embodiment. Device 600 may include some or all of the features of reader 505, for example. Device 600 is one example of a platform that is configured to provide a user input/output (I/O) interface and one or both of an IR transmitter (e.g., an LED or other light source) and an IR receiver (e.g., photodetector). Such a platform may further comprise processor logic to variously exchange respective signals with the user I/O interface and the IR transmitter and/or receiver. For example, the processor logic may receive a first signal based on user interaction with the user I/O interface and, based on the first signal, operate wireless communication logic of device 600 to transmit a wireless IR communication to an ophthalmic device (not shown). Alternatively or in addition, the wireless communication logic may send to the processor logic a second signal that is based on an IR communication received by device 600 from an ophthalmic device. Based on the second signal, the processor logic may provide an output via the user I/O interface.

In the embodiment shown, device 600 includes a bus 621 which interconnects components of device 600, such as the illustrative central processor 624, memory 627 (e.g., including one or more of random access memory, read only memory, flash memory, or the like), an input/output (I/O) controller 628, a user display 622, such as a display screen via a display adapter, or a touchscreen; a user input interface 626, which may include one or more controllers and associated user input devices such as a keyboard, mouse, touchscreen, and the like, and may be closely coupled to the I/O controller 628, fixed storage 623, such as a hard drive, flash storage, Fibre Channel network, storage area network (SAN) device, Small Computer System Interface (SCSI) device, and the like, and a removable media component 625 operative to control and receive an optical disk, flash drive, and the like. The device 600, in addition to a display device 622, may include outputs 632, such as speakers, a headphone jack, USB port and the like, that are controlled by the I/O controller 628. The device 600 may also include inputs 631 that may be connected to, for example, a microphone (not shown), a keyboard (not shown), an accelerometer (not shown) or similar device. The accelerometer, for example, may output a signal in response to a movement, such as shaking, of the device 600 to the bus 621. The outputted signal may be received and processed by the device 600. In an embodiment, device 600 further comprises an IR transmitter and/or an IR receiver—e.g., including the illustrative IR Tx/Rx 640—operated by I/O controller 628 or other such controller logic. IR Tx/Rx 640 may participate in a wireless communication between device 600 and a remote ophthalmic device such as one having IR communication features variously described herein.

The bus 621 allows data communication between the central processor 624 and the memory 627, which may include read-only memory (ROM) or flash memory (neither shown), and random access memory (RAM) (not shown), as previously noted. The RAM is generally the main memory into which the operating system and application programs are loaded. The ROM or flash memory can contain, among other code, the Basic Input-Output system (BIOS) which controls basic hardware operation such as the interaction with peripheral components. Applications resident with the device 600 are generally stored on and accessed via a device readable medium, such as a hard disk drive (e.g., fixed storage 623), an optical drive, floppy disk, or other storage medium 625.

The fixed storage 623 may be integral with the device 600 or may be separate and accessed through other interfaces. A network interface 629 may provide a direct connection to a remote server via a telephone link, to the Internet via an internet service provider (ISP), or a direct connection to a remote server via a direct network link to the Internet via a POP (point of presence) or other technique. The network interface 629 may provide such connection using wireless techniques, including digital cellular telephone connection, Cellular Digital Packet Data (CDPD) connection, digital satellite data connection or the like. For example, the network interface 629 may allow device 600 to communicate with one or more of a local area network, a wide area networks, an Internet, a cloud network and/or the like.

Many other devices or components (not shown) may be connected in a similar manner (e.g., document scanners, digital cameras and so on). Conversely, all of the components shown in FIG. 6 need not be present to practice the present disclosure. The components can be interconnected in different ways from that shown. The operation of a computerized device such as that shown in FIG. 6 may include processes adapted from techniques readily known in the art, which are not discussed in detail in this application. Code to implement the some embodiments can be stored in computer-readable storage media such as one or more of the memory 627, fixed storage 623, removable media 625, or on a remote storage location.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An ophthalmic device for implantation in an eye, the ophthalmic device comprising:
    an enclosure formed of a biocompatible material;
    control circuitry disposed in the enclosure and configured to sense a condition at the eye or to assist vision of the eye;
    wireless communication circuitry disposed in or on the enclosure, the wireless communication circuitry electrically coupled to the control circuitry, wherein the wireless communication circuitry includes:
        an optical receiver oriented to face a retina of the eye to detect first wireless signals from an external device outside of the eye after reflection off of the retina of the eye when the ophthalmic device is implanted into the eye, wherein the optical receiver is configured to detect the first wireless signals in an infrared band; and
        an optical transmitter oriented to face the retina of the eye when the ophthalmic device is implanted into the eye to emit second wireless signals for communicating with the external device outside of the eye via reflecting the second wireless signals off of the retina; and
    a dynamic optic positioned to assist vision of the eye when the ophthalmic device is implanted into the eye, wherein the dynamic optic is positioned to pass the first wireless signals incident into the eye prior to reflection off of the retina and pass the second wireless signals out of the eye after reflection off of the retina.

2. The ophthalmic device of claim 1, wherein the control circuitry is configured to selectively turn a functionality of the ophthalmic device on or off in response to the first wireless signals.

3. The ophthalmic device of claim 1, wherein the infrared band is between 700 nanometers (nm) and 2000 nm.

4. The ophthalmic device of claim 1, further comprising a pressure sensor disposed in or on the enclosure.

5. The ophthalmic device of claim 1, wherein the communication circuitry is to further exchange wireless communications between the ophthalmic device and another device, the wireless communications having a wavelength in a radio band.

6. The ophthalmic device of claim 1, wherein the ophthalmic device comprises an intraocular lens.

7. A system comprising:
    a base communication station; and
    an ophthalmic device for implantation in an eye, the ophthalmic device comprising:
        an enclosure formed of a biocompatible material;
        control circuitry disposed in the enclosure and configured to sense a condition at the eye or to assist vision of the eye;
        wireless communication circuitry disposed in or on the enclosure, the wireless communication circuitry electrically coupled to the control circuitry, wherein the wireless communication circuitry includes:
            an optical receiver oriented to face a retina of the eye to detect first wireless signals from the base communication station after reflection off of the retina of the eye when the ophthalmic device is implanted into the eye, wherein the optical receiver is configured to detect the first wireless signals in an infrared band; and
            an optical transmitter oriented to face the retina when the ophthalmic device is implanted into the eye to emit second wireless signals for communicating with the base communication station located outside of the eye via reflecting the second wireless signals off of the retina; and
        a dynamic optic positioned to assist vision of the eye when the ophthalmic device is implanted into the eye, wherein the dynamic optic is positioned to pass the first wireless signals incident into the eye prior to reflection off of the retina and pass the second wireless signals out of the eye after reflection off of the retina.

* * * * *